US012593829B2

(12) United States Patent
Edwards

(10) Patent No.: US 12,593,829 B2
(45) Date of Patent: Apr. 7, 2026

(54) ARTHROPOD BLOOD WARMING APPARATUS, SYSTEM AND METHOD

(71) Applicant: Lee County Mosquito Control District, Lehigh Acres, FL (US)

(72) Inventor: Travis J. Edwards, Lehigh Acres, FL (US)

(73) Assignee: Lee County Mosquito Control District, Lehigh Acres, FL (US)

( * ) Notice: Subject to any disclaimer, the term of this patent is extended or adjusted under 35 U.S.C. 154(b) by 0 days.

(21) Appl. No.: 17/382,048

(22) Filed: Jul. 21, 2021

(65) Prior Publication Data

US 2023/0035230 A1      Feb. 2, 2023

(51) Int. Cl.
*A01K 67/30*      (2025.01)

(52) U.S. Cl.
CPC ................................... *A01K 67/30* (2025.01)

(58) Field of Classification Search
CPC .............................. A01K 67/033; A01K 67/30
See application file for complete search history.

(56) References Cited

U.S. PATENT DOCUMENTS

| | | | | | |
|---|---|---|---|---|---|
| 4,167,663 | A | * | 9/1979 | Granzow, Jr. ........... | A61M 5/44 604/245 |
| 4,707,587 | A | * | 11/1987 | Greenblatt .............. | A61M 5/44 219/400 |
| 4,850,305 | A | * | 7/1989 | Georgi ................. | A01K 67/033 119/303 |
| 5,983,557 | A | * | 11/1999 | Perich ................. | A01M 1/2044 43/132.1 |

| | | | | | |
|---|---|---|---|---|---|
| 6,708,443 | B2 | * | 3/2004 | Hall ........................ | A01M 1/02 43/132.1 |
| 7,229,627 | B2 | | 6/2007 | Hoffman et al. | |
| 7,281,350 | B2 | * | 10/2007 | Wilbanks ................ | A01M 1/04 43/107 |
| 7,434,351 | B2 | * | 10/2008 | Bette ..................... | A01M 1/106 43/107 |
| 7,448,160 | B2 | * | 11/2008 | Roberts ................... | A01M 1/02 43/132.1 |
| 7,694,455 | B1 | * | 4/2010 | Bowden ................ | A01M 1/106 43/132.1 |
| 8,109,035 | B2 | * | 2/2012 | Bowden ................ | A01M 1/106 43/132.1 |
| 9,265,247 | B2 | * | 2/2016 | Gaugler ................. | A01N 25/00 |
| 10,258,027 | B2 | * | 4/2019 | Gaugler ................. | A01N 25/24 |
| 11,429,683 | B1 | | 8/2022 | Lin | |

(Continued)

FOREIGN PATENT DOCUMENTS

CN        202374895        8/2012

OTHER PUBLICATIONS

U.S. Appl. No. 15/050,679, filed Aug. 24, 2017, Ueti et al.

*Primary Examiner* — Monica L Perry
*Assistant Examiner* — Aaron M Rodziwicz
(74) *Attorney, Agent, or Firm* — Kelly G. Swartz; Widerman Malek, PL

(57) ABSTRACT

An arthropod blood warming apparatus, system and method includes a control unit, at least one thermal cell, at least one container for holding human or animal blood, and a thin layer of film capable of being punctured by the proboscis of an arthropod over each container. Arthropods such as mosquitoes are attracted to the warm blood and thereby encouraged to consume such blood that is necessary for egg production.

7 Claims, 6 Drawing Sheets

(56) References Cited

U.S. PATENT DOCUMENTS

| | | | |
|---|---|---|---|
| 11,432,538 B1* | 9/2022 | Stoddard | B33Y 80/00 |
| 2005/0274061 A1* | 12/2005 | Zhu | A01M 1/06 |
| | | | 43/132.1 |
| 2006/0090391 A1* | 5/2006 | Huang | A01M 1/106 |
| | | | 43/107 |
| 2007/0074447 A1* | 4/2007 | Kalogroulis | A01M 1/106 |
| | | | 43/107 |
| 2007/0082164 A1* | 4/2007 | Sellers | A47J 36/34 |
| | | | 428/167 |
| 2007/0157508 A1* | 7/2007 | Chang | A01M 1/06 |
| | | | 43/107 |
| 2007/0169209 A1* | 7/2007 | Hoffman | A01K 67/033 |
| | | | 800/13 |
| 2010/0083562 A1* | 4/2010 | Fukuhara | A01M 1/106 |
| | | | 43/107 |
| 2017/0238513 A1* | 8/2017 | Ueti | A01K 67/033 |
| 2018/0014513 A1* | 1/2018 | Mascari | A01M 1/023 |

* cited by examiner

100

ARTHROPOD BLOOD WARMING APPARATUS, SYSTEM AND METHOD

BACKGROUND OF THE INVENTION

Arthropods—particularly mosquitos—are a constant source of irritation and potential disease transmission for humans and other mammals. Critically, ever since the US Army Yellow Fever Commission's 1901 publications of experimental data showing that yellow fever was transmitted by mosquito bite, tropical disease control has focused on mosquito eradication.

In order to effectively conduct mosquito research—including the testing of various insecticides—large numbers of mosquitos need to be bred in laboratory settings, i.e., in controlled environments where there is no risk that such mosquitos will become infectious disease carriers. This can be particularly important in testing anti-larval chemicals given the logistic difficulties of identifying and isolating larval mosquito populations in the wild.

Laboratory breeding of mosquitoes poses a number of challenges; including that most mosquito species require a blood meal in order to begin the process of egg development. Experimentation has shown, however, that mosquitos will not ingest blood which is not kept at approximately body temperature. Historically, many laboratories would expose (unlucky) personnel directly to mosquitoes in order to provide a body-temperature source of blood—with such personnel often directed to place a hand or atm inside an enclosure to allow mosquitos to feed. Self-evidently, this is extremely uncomfortable to such personnel (and could pose a source of illness in the event that one or more of the mosquitos were inadvertently exposed to a pathogen). Some references concerning blood warming apparatuses include the following, but none disclose an arthropod blood warming system having the same structure as the instant invention:

(i) U.S. Pat. No. 4,167,663 (Granzow, Jr., et al.) entitled "Blood warming apparatus";

(ii) U.S. Pat. No. 4,707,587 (Greenblatt) entitled "Blood warming method and apparatus using gaseous heat exchange medium";

(iii) U.S. Ser. No. 11/429,683 (Dancy) entitled "Mosquito breeding trap and method for eliminating mosquitoes";

(iv) U.S. Pat. No. 7,229,627 (Hoffman et al.) entitled "Apparatuses and methods for the production of haematophagous organisms and parasites suitable for vaccine production";

(v) CN202374895 (Zhao et al.) entitled "Indoor mosquito breeding device";

(vi) U.S. Pat. No. 8,109,035 (Bowden et al.) entitled "Apparatus and method of mosquito control"; and (vii) U.S. Ser. No. 15/050,679 (Ueti et al.) entitled "In vitro parasite feeding system".

SUMMARY OF THE INVENTION

This invention relates to an arthropod blood warming apparatus, system and method of using same. More particularly, the instant invention relates to:

(i) an arthropod blood warming apparatus for use in feeding blood to arthropods (such as mosquitoes) comprising: (a) a control unit; (b) at least one thermal cell; (c) at least one container for holding blood; and (d) (optionally) a thin layer of film over such containers, said film capable of being punctured by the proboscis of an arthropod such as a mosquito;

(ii) an arthropod blood warming system comprising: (a) a plurality of arthropod blood warming apparatuses; (b) a power source; and (c) a controlled environment wherein a plurality of arthropods are located; and (iii) an arthropod blood warming method comprising: (a) placing human or animal blood in at least one arthropod warming apparatus connected to a power source; (b) selecting a desired blood temperature using a control unit; (c) warming the blood using a heating element until such blood reaches the desired temperature; (d) maintaining the temperature of the blood using a thermostat (e.g., along a pre-defined temperature/time hysteresis curve using a thermal sensor connected to a microprocessor); and (e) exposing the heated blood to arthropods (e.g., mosquitos) and allowing such arthropods to feed on same.

The primary object of the present invention is to provide a means of mimicking the body and skin temperature of a mammal in order to attract arthropods—particularly mosquitoes—to consume such blood.

Another object of the present invention is to provide a system and method for warming blood in order to attract arthropods—particularly mosquitoes—to consume such blood so that the arthropods will lay eggs, e.g., to breed such arthropods under laboratory conditions. Based on experimental research, a blood temperature range of 90 to 102 degrees Fahrenheit is most effective.

The present invention fulfills the above and other objects by providing a system (and corresponding method of use) for heating human or animal blood. More specifically, this system includes: (a) an electrical control unit whereby the temperature of the blood can be selected from within a pre-defined range of temperatures; (b) at least one thermal cell further comprising a heating element; (c) at least one container for holding blood; and (d) optionally, a thin layer of film (which simulates skin) over such container, said thin layer of film comprised of a material capable of being punctured by the proboscis of an arthropod (e.g., a mosquito).

BRIEF DESCRIPTION OF THE DRAWINGS

In the following detailed description, reference will be made to the attached drawings in which.

REFERENCE NUMERAL CHART

Figures 1A, 1B, 1C:
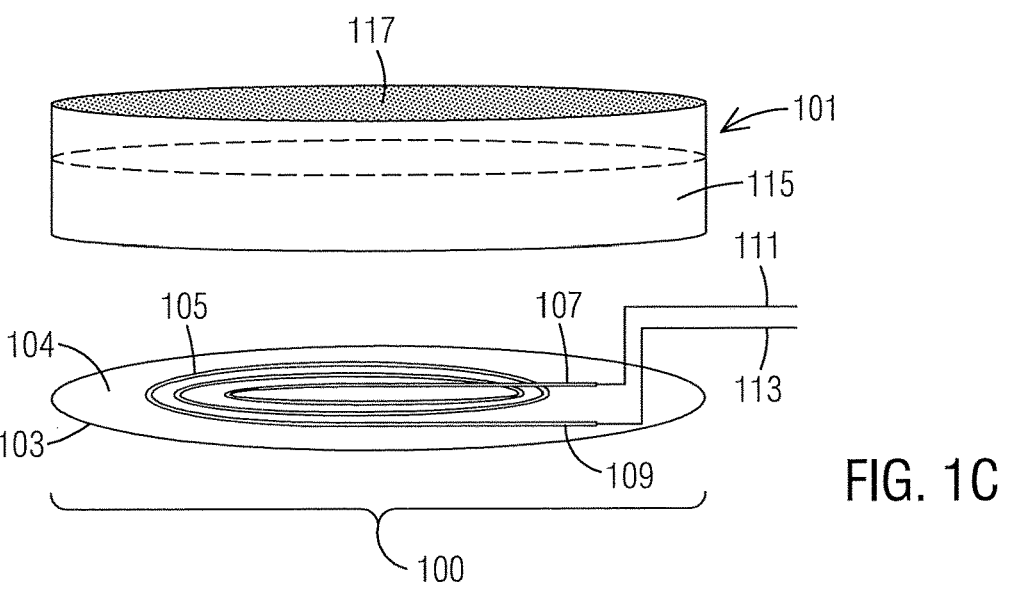
FIG. 1A is a simplified perspective view of an embodiment of an arthropod blood warming apparatus.
FIG. 1B is a simplified perspective view of another embodiment of an arthropod blood warming apparatus.
FIG. 1C is a simplified perspective view of another embodiment of an arthropod blood warming apparatus.

For purposes of describing the preferred embodiment, the terminology used in reference to the number components in the drawings is as follows:

| 100 | Arthropod Blood Warming Apparatus |
|-----|-----------------------------------|
| 101 | Container |
| 103 | Thermal Cell |
| 104 | Heat Resistant Mat |
| 105 | Heating Coil (also called an "Electric Heating Element") |
| 107 | Positive Coil Terminal |
| 109 | Negative Coil Terminal |
| 111 | Positive Outlet Terminal |
| 113 | Negative Outlet Terminal |
| 115 | Blood |
| 117 | Film |
| 119 | Power Coupling |
| 121 | Control Unit |
| 123 | Power Source |
| 125 | Temperature Probe |
| 127 | Mounting Plate |
| 129 | Control Module |
| 131 | Power Input Socket |
| 133 | Terminal Block |
| 135 | Grips |

DETAILED DESCRIPTION OF THE INVENTION

FIG. 1A is a simplified perspective view of an Arthropod Blood Warming Apparatus 100. As shown in FIG. 1A, the Arthropod Blood Warming Apparatus 100 has a Container 101 with a Thermal Cell 103. In one embodiment, the Container 101 could be a standard Petri dish (with the Thermal Cell 103 dimensionally sized to fit within a standard Petri dish) or a circular, concave piece of glass (e.g., using a watch glass). FIG. 1A shows the Thermal Cell 103 inside the Container 101. In alternative embodiments, the Thermal Cell 103 could be placed on the exterior of the Container 101 or be formed integral to the Container 101. The Thermal Cell 103 could be constructed of any material which fairly conducts heat without damage, e.g., silicone. Each Thermal Cell 103 has at least one Heating Coil 105. The Heating Coil 105 has a Positive Coil Terminal 107 and a Negative Heating Terminal 109 which are electrically connected to a Positive Outlet Terminal 111 and a Negative Outlet Terminal 113, respectively. In one embodiment, the Positive Outlet Terminal 111 and the Negative Outlet Terminal 113 could be part of a coaxial cable connector (not shown). A quantity of human or animal Blood 115 is inside the Container 101. When an electric current is applied to the Heating Coil 105, the resistivity of the Heating Coil 105 causes said Heating Coil 105 to heat. This thermal energy is transferred to the Blood 115, raising the temperature of said Blood 115. Based on experimental research, a blood temperature range of 90 to 102 degrees Fahrenheit is most effective. A thin Film 117 covers the Container. The Film 117 comprises a material capable of being punctured by the proboscis of an arthropod such as a mosquito. In one embodiment, the Film 117 is comprised of a moisture-proof, self-sealing film such as PARAFILM® "M" brand laboratory film.

FIG. 1B is a simplified perspective view of an alternative embodiment of an Arthropod Blood Warming Apparatus 100. As shown in FIG. 1B, the Arthropod Blood Warming Apparatus 100 is comprised of: (a) a Container 101; and (b) a Thermal Cell 103; said Container 101 and Thermal Cell 103 being readily detachable from one another (FIG. 1B shows the Container 101 detached from the Thermal Cell 103). A heat-conducting medium could be included within the Thermal Cell 103.

FIG. 1C is a simplified perspective view of an alternative embodiment of an Arthropod Blood Warming Apparatus 100. As shown in FIG. 1C, the Arthropod Blood Warming Apparatus 100 is comprised of: (a) a Container 101; and (b) a Thermal Cell 103; said Container 101 and Thermal Cell 103 being readily detachable from one another (FIG. 1B shows the Container 101 detached from the Thermal Cell 103) with the Container capable of being set atop the Thermal Cell 103. In the embodiment shown in FIG. 1C, each Thermal Cell 103 is comprised of a Heat Resistant Mat 104 with at least one embedded Heating Coil 105. The Heat Resistant Mat 104 should consist of some heat resistant material (e.g., silicone). Experimentation has shown that a two millimeter (2 mm) thick piece of silicone works well for the Heat Resistant Mat 104 inasmuch as said thickness promotes heat resistance and helps hold the heating wire in form, i.e., helps prevent deformation of the Thermal Cell 103. The Heat Resistant Mat 104 also helps direct radiant heat towards and away from the base and towards the Container 101 when the Container 101 is placed atop the Thermal Cell 103. Heat resistant Grips 135 may optionally be included on a surface of the Thermal Cell 103. The Grips 135 should consist of some flexible, heat resistant material (e.g., silicone). Such Grips 135 help hold the Container 101 in place atop the Thermal Cell 103.

In certain embodiments (not shown), the Thermal Cell 103 comprises a concaved ring (e.g., constructed of plastic such as polylactide ("PLA")) that contours to the curvature of the Container 101 (e.g., contouring to the curvature of a glass petri dish). A film of silicone is then adhered to the plastic (e.g., using self-etching superglue)

Figure 2A:
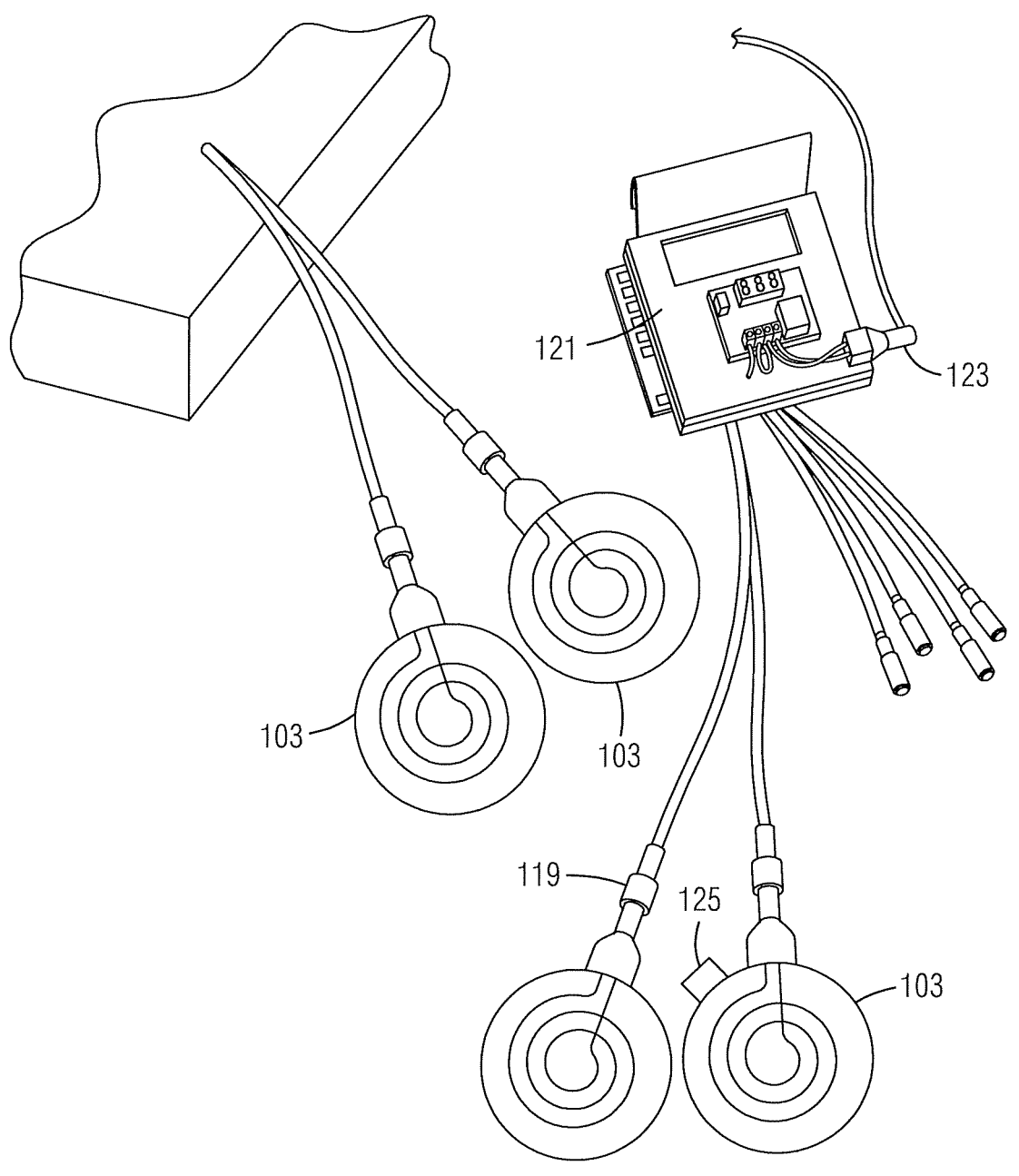
FIG. 2A is a perspective view of multiple thermal cells connected to a control system.
Figure 2B:
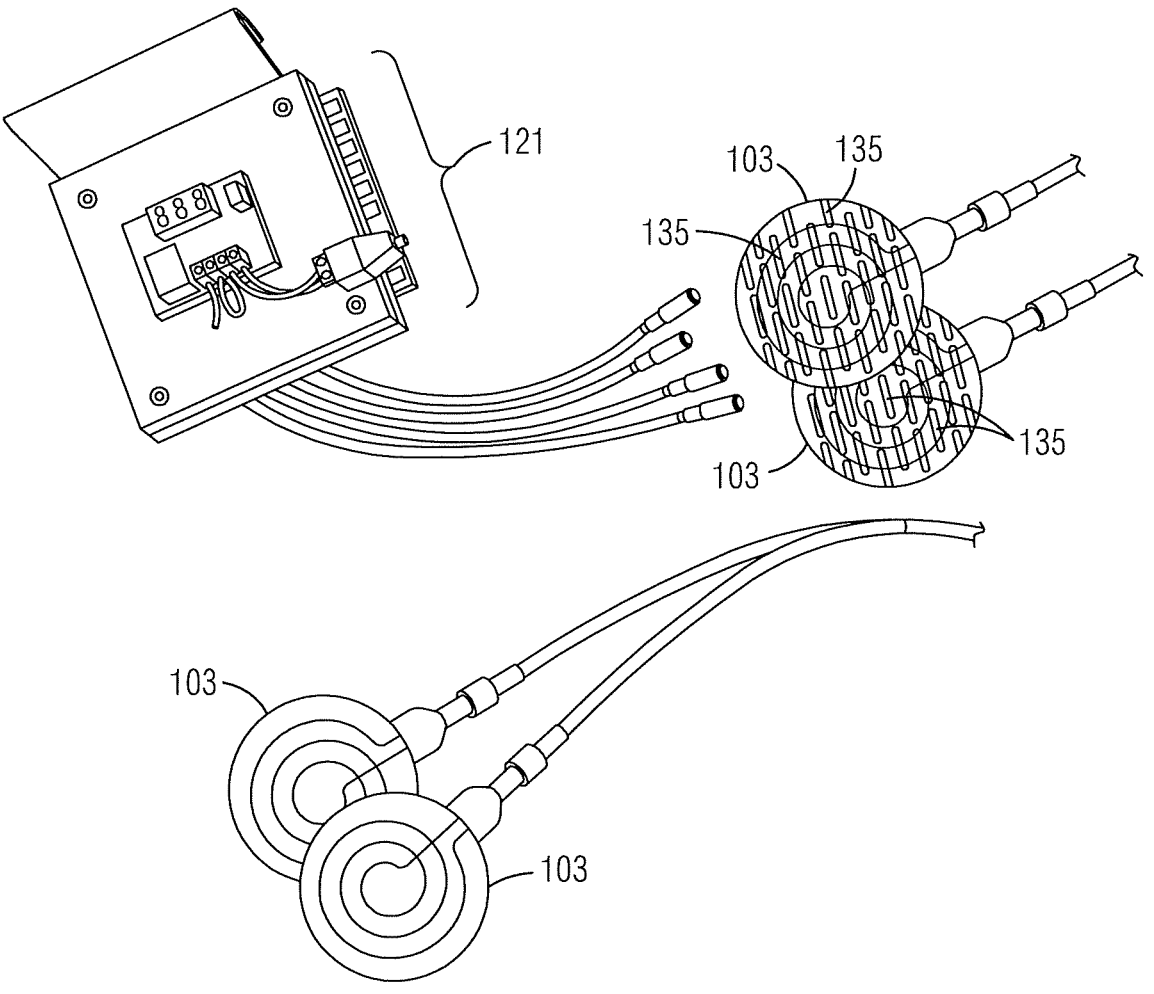
FIG. 2B is a perspective view of multiple thermal cells connected to a control system.

FIGS. 2A and 2B are perspective views of multiple Thermal Cells 103 connected to a Control System 121. As shown in FIG. 2A, each Thermal Cell 103 has a Power Coupling 119 (which includes a Positive Outlet Terminal 111 (not shown) and a Negative Outlet Ten final 113 (not shown)). The Power Couplings 119 are electrically connected to a Control Unit 121. At least one Temperature Probe 125 is also connected to the Control Unit 121. In the embodiment shown in FIG. 2A, a single, common Temperature Probe 125 is used to regulate the temperature of several Thermal Cells 103. In alternative embodiments, however, a separate Temperature Probe 125 could be used for each individual Thermal Cell 103.

Figure 3:
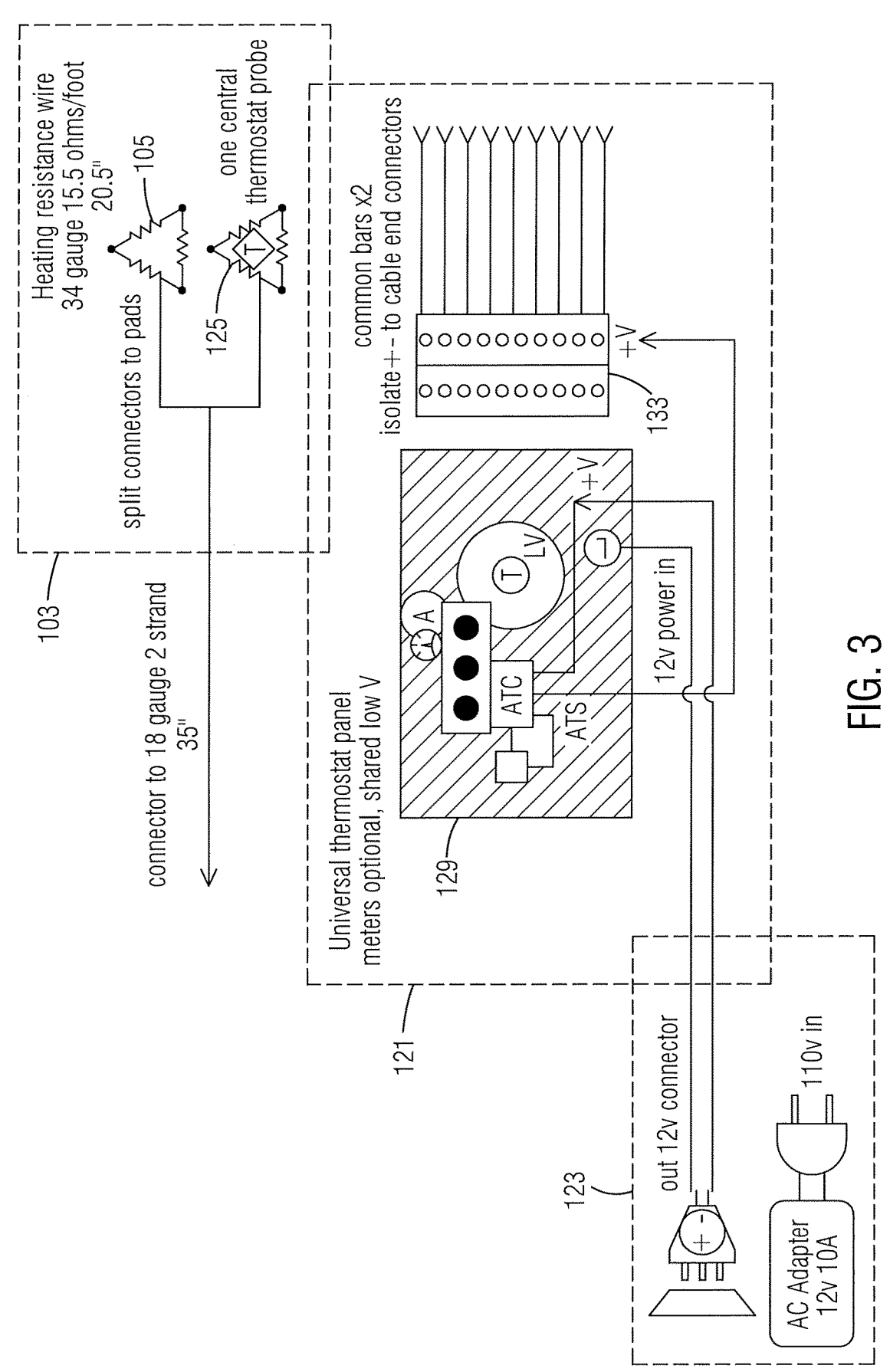
FIG. 3 is a simplified wiring diagram of an arthropod blood warming apparatus.

FIG. 3 is a simplified wiring diagram of an Arthropod Blood Warming Apparatus 100. As shown in FIG. 3, the Control Unit 121 is electrically connected to a Power Source 123. The Control Unit 121 is comprised of a Control Module 129 (e.g., a standard thermostat temperature controller switch module) having a control input for a Temperature Probe 125 (not shown). The Control Unit 121 further comprises a Terminal Block 133 to which cables (that are electrically connected to the Positive Outlet Terminals 111 and Negative Outlet Terminals 113 of each Thermal Cell 103). Within a Thermal Cell 103, a Heating Coil 105 converts electrical energy into heat energy (through Ohm's law). A Temperature Probe 125 can then be used to provide control input for the Control Module 129, i.e., the Temperature Probe 125 sends temperature readings to the Control Module 129 where such readings are used to modulate (including turning on and off) the current delivered to the Heating Coil 105.

Figure 4A:
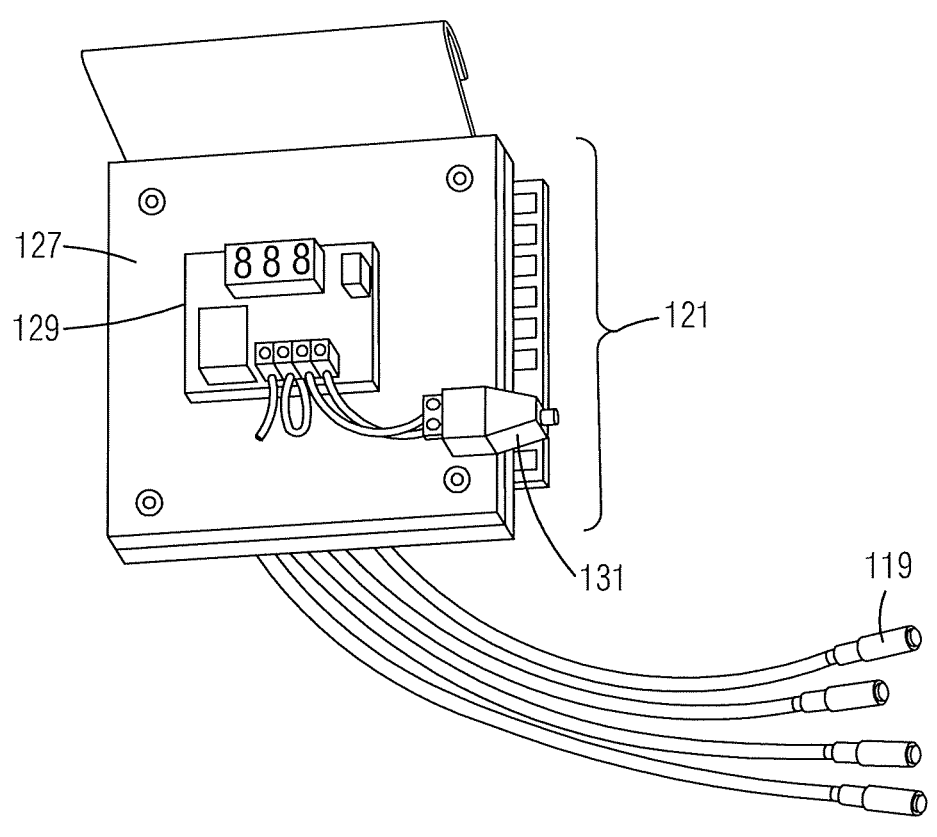
FIG. 4A is a top view of a control unit.
Figure 4B:
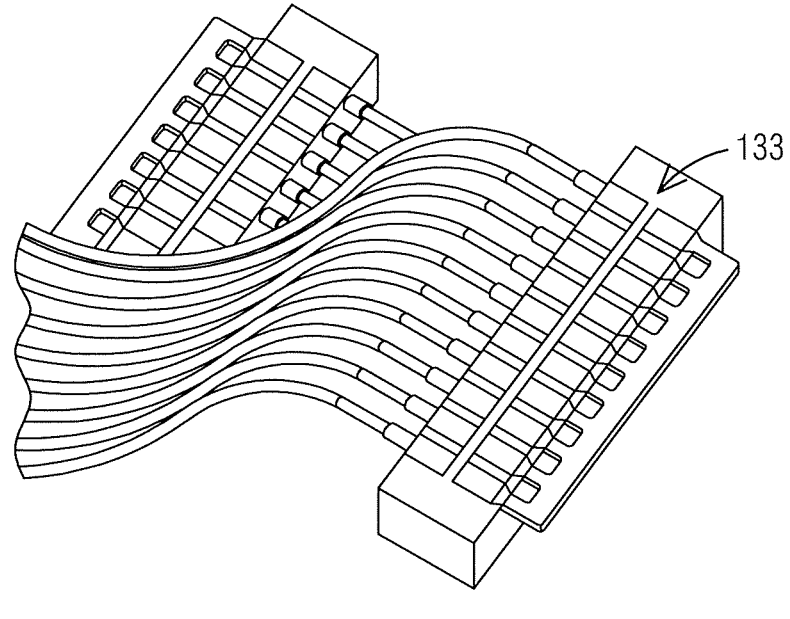
FIG. 4B is a bottom view of a control unit.

FIGS. 4A and 4B show a top view and a bottom view, respectively, of a control unit. As shown in FIG. 4A, a Control Module 129 is affixed to a Mounting Plate 127 (said Mounting Plate 127 made of a non-conductive material). A Power Input Socket 131 is likewise affixed to a Mounting Plate 127 and electrically connected to the Control Module 129. A plurality of cables are attached to the Control Unit 121 using a Terminal Block 133 as shown in FIG. 4B (not shown in FIG. 4A). Each of these cables has a Power Coupling 119 on the distal end of the cable in order to readily, electrically connect same to one or more Thermal Cells 103.

Figure 5:
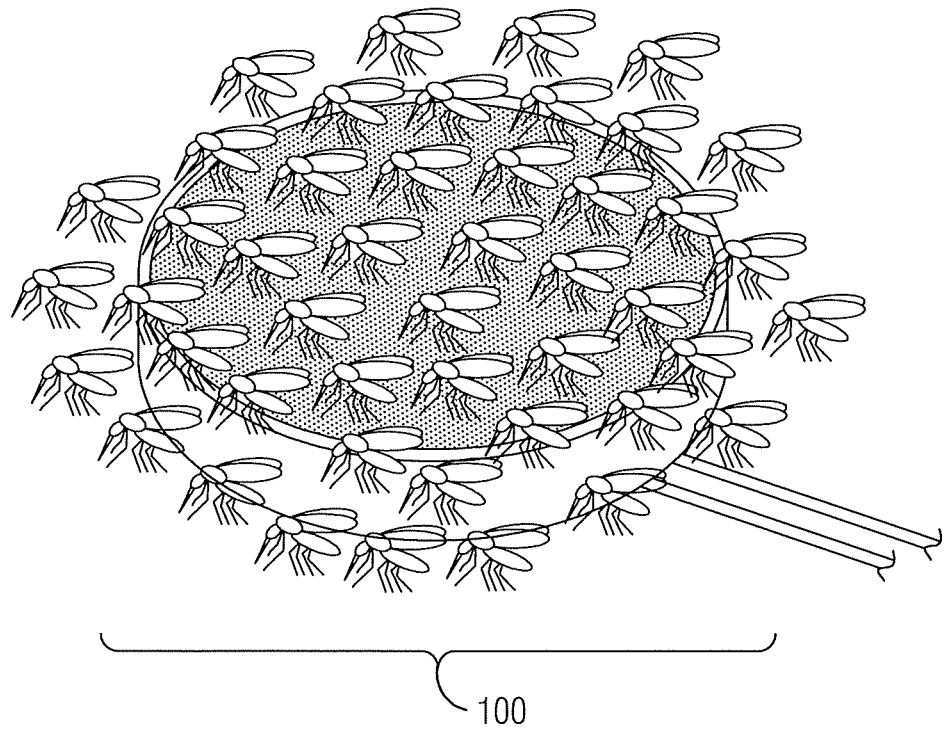
FIG. 5 is a perspective view showing an arthropod blood warming apparatus in use in connection with a plurality of mosquitos.

FIG. 5 is a perspective view showing an Arthropod Blood Warming Apparatus 100 in use in connection with a plurality of mosquitos. As can be seen in FIG. 4, mosquitoes land on the Film 117. Each mosquito then punctures the Film 117 with its proboscis in order to drink warmed Blood 115. Experimentation using the instant Arthropod Blood Warming Apparatus 100 in connection with mosquitos has shown a nearly one-thousand percent (1,000%) increase in mosquito egg production, namely, approximately 10,000 eggs were harvested from a dish of un-warmed blood, while approximately 1,000,000 eggs were harvested from a dish of blood warmed using an Arthropod Blood Warming Apparatus 100.

Each Arthropod Blood Warming Apparatus 100 may be calibrated by using water or another liquid in place of blood. First, limiting temperatures are set and checked for a few cycles to set a blood temperature range and the range is refined down to mimic body temperature by adjusting the varying degree of deviation range in the circuit parameter.

It is to be understood that while a preferred embodiment of the invention is illustrated, it is not to be limited to the specific form or arrangement of parts herein described and shown. It was be apparent to those skilled in the art that various changes may be made without departing from the scope of the invention and the invention is not to be considered limited to what is shown and described in the specification and drawings.

Having thus described my invention, I claim:

1. An arthropod blood warming apparatus comprising:
   a control unit;
   thermal cell comprising a heating coil electrically connected to the control unit and in thermal communication with a container;
   the container being configured to hold blood;
      a temperature probe co-located with the heating coil, wherein the temperature probe provides a temperature reading to the control unit; and
      a thin layer of film over the container, said film capable of being punctured by the proboscis of an arthropod; and
   wherein the temperature reading is utilized by the control unit to modulate a current delivered to the heating coil.

2. The arthropod blood warming apparatus of claim 1, wherein:
   the thermal cell further comprises a heat resistant mat wherein the heating coil is embedded in the heat resistant mat.

3. The arthropod blood warming apparatus of claim 1, wherein:
   the control unit comprises a temperature controller microprocessor having an input adapted to receive the temperature reading from the temperature probe.

4. The arthropod blood warming apparatus of claim 3, further comprising:
   a plurality of containers;
   a plurality of temperature probes;
   a plurality of thermal cells, wherein each of the plurality of temperature probes is co-located with one of the plurality of thermal cells, each of the thermal cells is in thermal communication with one of the plurality of containers; and
   wherein the control unit has a plurality of power couplings wherein each of the plurality of power couplings is connected to one of the plurality of thermal cells.

5. The arthropod blood warming apparatus of claim 1, wherein:
   the thin layer of film comprises self-sealing film.

6. The arthropod blood warming apparatus of claim 1, wherein:
   the thermal cell further comprises a heat resistant mat;
   wherein the heating coil is embedded in the heat resistant mat;
   wherein the heat resistant mat has a plurality of heat resistant grips;
   the control unit comprises a temperature controller microprocessor having an input for the temperature probe and a power coupling connected to the thermal cell; and
   the thin layer of film comprises self-sealing film.

7. An arthropod blood warming apparatus comprising:
   a control unit;
   a plurality of thermal cells wherein each of the plurality of thermal cells comprises:
      a heating coil electrically connected to the control unit and in thermal communication with one of a plurality of containers;
   wherein each of the plurality of containers is configured to hold blood;
   a temperature probe co-located with one of the plurality of heating coils, wherein the temperature probe provides a temperature reading to the control unit; and
   a plurality of thin layers of film, wherein one of the plurality of thin layers of film is positioned over each of the plurality of containers, wherein each of the plurality of thin layers of film is capable of being punctured by the proboscis of an arthropod; and
   wherein the temperature reading is utilized by the control unit to modulate a plurality of currents, wherein each of the plurality of currents is delivered to one of the plurality of heating coils.

\* \* \* \* \*